(12) United States Patent
McQueen

(10) Patent No.: US 6,491,038 B1
(45) Date of Patent: Dec. 10, 2002

(54) PHYSICAL RESTRAINING PAD ASSEMBLY AND SYSTEM

(76) Inventor: Angus A. McQueen, 348 Raymond St., Mocksville, NC (US) 27028

( * ) Notice: Subject to any disclaimer, the term of this patent is extended or adjusted under 35 U.S.C. 154(b) by 0 days.

(21) Appl. No.: 09/975,790

(22) Filed: Oct. 11, 2001

(51) Int. Cl.[7] .............................................. A61B 19/00
(52) U.S. Cl. ........................ 128/869; 128/870; 128/872
(58) Field of Search .................. 128/845, 846, 128/869, 870, 872, 874, 875; 5/624, 625, 628; 70/16

(56) References Cited

U.S. PATENT DOCUMENTS

| | | | | |
|---|---|---|---|---|
| 2,766,751 A | * | 10/1956 | Topa | 128/870 |
| 3,476,107 A | * | 11/1969 | Matt | 128/870 |
| 4,852,587 A | * | 8/1989 | Share | 128/870 |
| 5,121,514 A | * | 6/1992 | Rosane | 5/628 |
| 5,402,753 A | * | 4/1995 | Barnes | 128/870 |
| 5,829,443 A | * | 11/1998 | Cunningham | 70/16 |

* cited by examiner

Primary Examiner—Michael A. Brown
(74) Attorney, Agent, or Firm—Adams, Schwartz & Evans, P.A.

(57) ABSTRACT

A physical restraining pad assembly including a pad constructed of a flexible, breathable material of a size and shape to cover the body of an individual with arms outstretched. An outer mesh covering encloses the pad. A plurality of spaced handles are positioned on a back side of the pad for use by an attendant. The pad has a viewing window of a size and shape to allow the attendant to see through the pad for observing the individual being restrained. Complementary touch fasteners on a pair of such pads may be used by two attendants to restrain an individual between them. A single pad with complementary touch fasteners on opposing sides may be used to restrain an individual by wrapping the individual within the pad with the complementary touch fasteners engaged with each other.

21 Claims, 6 Drawing Sheets

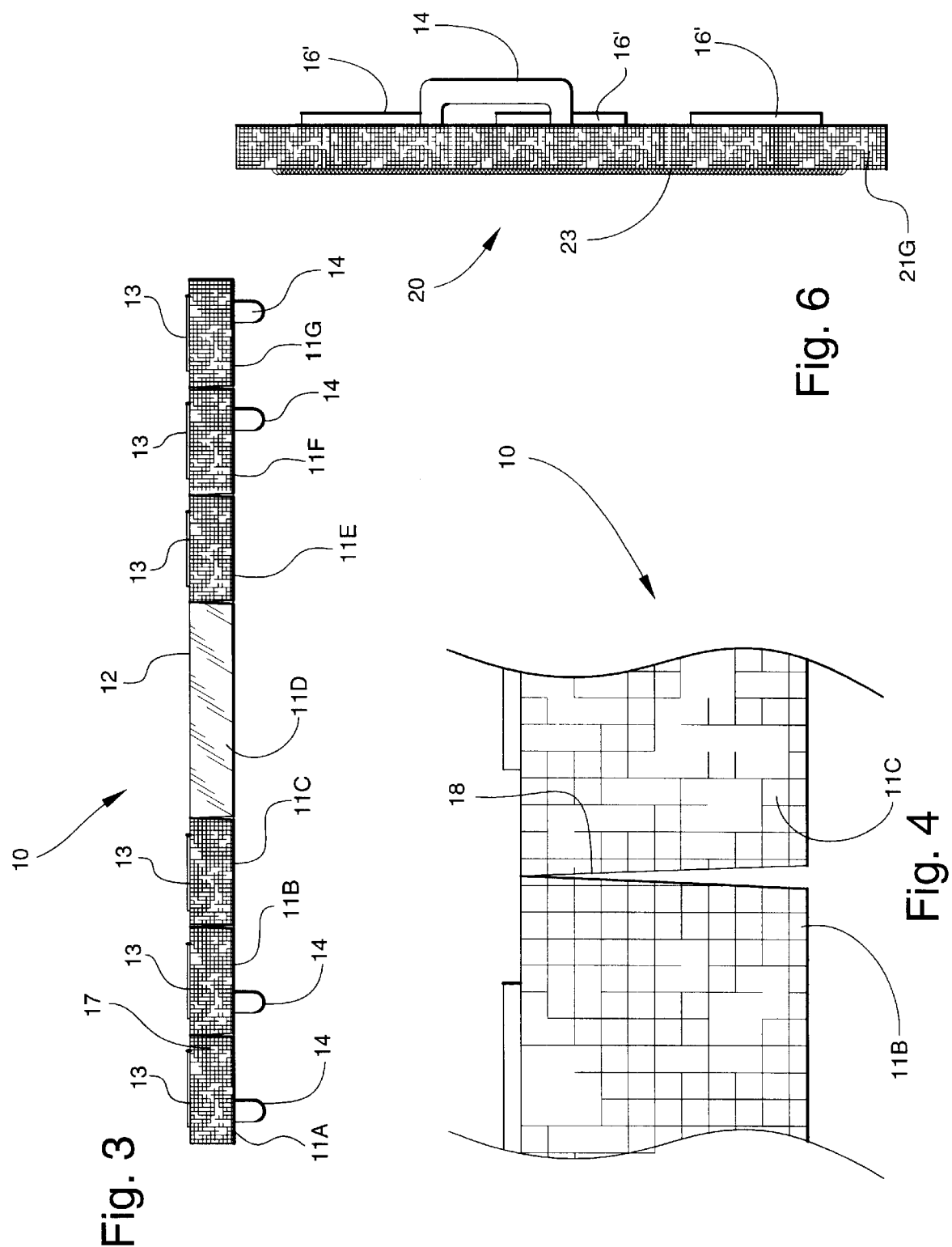

PHYSICAL RESTRAINING PAD ASSEMBLY AND SYSTEM

TECHNICAL FIELD AND BACKGROUND OF THE INVENTION

This invention relates to a physical restraining pad assembly and system. It is often necessary to employ a physical restraint device to restrain an individual who becomes violent for one reason or another to prevent that individual from hurting himself or others. Physical restraint systems are commonly practiced in prisons, mental institutions, and other facilities as well as in public, i.e., to effect arrests or involuntary immobilizations. Because physical restraint is usually required under less than ideal circumstances involving either or both an agitated, violent individual and one or more cautious yet apprehensive attendants, problems may arise when restraint is attempted. One such problem is injury to the attendant due to uncontrolled, violent and forceful movements of the individual being restrained. This invention provides protection to attendants through padding and, optionally, impact-resistant kick protection panels. This invention protects the restrained individual from suffocation because the pad is completely breathable. Also, once an individual is restrained, escape is a concern.

Touch fasteners of various designs, strengths and structures have variable and predictable resistance to shear and peel forces and have been found suitable by applicant for application to this invention. These touch fasteners are also usable as "stops" or "brakes" to provide a guard against escape of the individual once restrained.

Additionally, stops of touch fastener material may be placed along the pad to provide a guard against escape of the individual once restrained. Finally, because of the volatile circumstances giving rise to the need to physically restrain an individual, restraint attempts may be unsuccessful. Furthermore, a large surface area of each pad is covered by touch fasteners to ensure that any contact between two complementary pads will result in a bond with out regard to the alignment or orientation of one pad relative to the other.

SUMMARY OF THE INVENTION

Therefore, it is an object of the invention to provide a physical restraining pad assembly.

It is another object of the invention to provide a physical restraining pad assembly that is easy to use in order to restrain an individual.

It is another object of the invention to provide a physical restraining pad assembly that provides kick-protection to the attendant when restraining a violent individual.

It is another object of the invention to provide a physical restraining pad assembly that provides head protection to the restrained individual.

It is another object of the invention to provide a physical restraining pad assembly that is breathable to prevent suffocation of the restrained individual.

It is another object of the invention to provide a physical restraining pad assembly that may be used for different purposes by placing different inserts in a pocket in the outer mesh.

It is another object of the invention to provide a physical restraining pad assembly to provide a bullet proof pad for use in crowd control.

It is another object of the invention to provide a physical restraining pad assembly that is suitable for use by different attendants through the availability of different handle positions.

It is another object of the invention to provide a physical restraining pad assembly that gives the attendant visibility of the violent individual on the other side upon approach while still maintaining the protection of the pad.

It is another object of the invention to provide a physical restraining pad assembly that affords a great probability of successfully restraining an individual due to a large surface area of touch fasteners that form bonds with complimentary touch fasteners when the two come into contact.

It is another object of the invention to provide a physical restraining pad assembly that provides kick-protection and punch-protection to the attendant when restraining a violent individual. The invention makes it possible to provide this protection in varying thicknesses, weights and resiliences, as desired by the customer and as required by the intended application.

It is another object of the invention to provide a physical restraining pad assembly that may be used for different purposes by placing different layers on top of or behind the basic pad assembly. These may be fixed in place as needed by touch fasteners, rivets, grommets, zippers or such other devices as may prove effective.

It is another object of the invention to provide a physical restraining pad assembly which includes a bullet-proof pad for use in crowd control, hostage, barricade or sniper situations.

It is another object of the invention to provide a pad assembly which includes a mesh covering within which varying layers of shock absorbent materials are contained, and, to the covering are attached additional layers of specialized materials for accomplishing additional tasks such as bullet and missile protection.

These and other objects of the present invention are achieved in the preferred embodiments disclosed by providing a physical restraining pad assembly including a pad constructed of a flexible, breathable material of a size and shape to cover the body of an individual with arms outstretched. An outer mesh covering encloses the pad. A plurality of spaced handles are positioned on a back side of the pad for use by an attendant. The pad has a viewing window of a size and shape to allow the attendant to see through the pad for observing the individual being restrained.

According to one preferred embodiment of the invention, the plurality of spaced handles are positioned to accommodate varying arm lengths and heights of different attendants.

According to another preferred embodiment of the invention, the pad includes a supplemental head restraining pad positioned adjacent to a top edge of the pad to provide head protection for the individual when restrained.

According to yet another preferred embodiment of the invention, the pad is constructed of fire-retardant materials.

According to yet another preferred embodiment of the invention, the pad of flexible, breathable material is constructed of a plurality of overlaid layers. The overlaid layers include a layer of dense matting to provide rigidity to the pad and protection for the attendant against movement of the individual, a layer of soft matting to promote flexibility of the pad, and an inner layer of mesh to fix the layers and to promote breathability of the pad.

According to yet another preferred embodiment of the invention, the pad includes a plurality of pieces of impact-resistant Styrofoam spaced apart from each other along the width and length of the pad within the outer mesh covering of the pad to provide additional kick protection to the attendant while maintaining breathability;

According to yet another preferred embodiment of the invention, the pad includes a pocket positioned within the outer mesh covering of the pad on the back side thereof for receiving one or more supplemental inserts.

According to yet another preferred embodiment of the invention, a supplemental insert is a bulletproof panel.

The objects of the present invention are also achieved in the preferred embodiments disclosed by providing a physical restraining pad assembly for use in restraining a violent individual including a first pad constructed of a flexible, breathable material of a size and shape to cover the body of an individual with arms outstretched. The first pad includes, an outer mesh covering enclosing the entire pad, touch-fasteners on a front side of the first pad, a plurality of spaced handles positioned on a back side of the first pad for use by a first attendant, and a viewing window of a size and shape to allow the first attendant to see through the first pad for observing the individual being restrained. A complementary second pad is constructed of a flexible, breathable material of size and shape to cover the body of an individual with arms outstretched for use in conjunction with the first pad in order to confine a violent individual. The complementary second pad includes an outer mesh covering enclosing the entire pad, complementary touch fasteners on a front side of the complementary second pad, a plurality of handles positioned on a back side of the complementary second pad for use by a second attendant, and a viewing window of a size and shape to allow the second attendant to see through the complementary second pad for observing the individual being restrained.

The first pad is manoevered by the first attendant and the complementary second pad is manoevered by the second attendant to sandwich a violent individual therebetween such that the touch fasteners on the back side of the first pad and the complementary touch fasteners on the back side of the complementary second pad meet to form a bond of sufficient strength to restrain the individual within the remaining space between the two pads where the touch fasteners are not in contact.

According to one preferred embodiment of the invention, the plurality of handles are positioned to accommodate varying arm lengths and heights of users.

According to another preferred embodiment of the invention, the physical restraining pad assembly includes a supplemental head restraining pad positioned adjacent to a top edge of each pad to provide head protection for the individual when restrained.

According to yet another preferred embodiment of the invention, the touch fasteners include spaced-apart strips of touch fasteners located on the front side of the first pad and the complementary touch fasteners include spaced-apart strips of complementary touch fasteners located on the front side of the complementary second pad, positioned to mate with the spaced-apart strips of touch fasteners when the two pads are pressed together.

According to yet another preferred embodiment of the invention, the touch fasteners include vertically spaced strips of touch fasteners that occupy at least fifty percent of the surface area of the front side of the first pad and the complementary touch fasteners include horizontally spaced strips of complementary touch fasteners that occupy at least fifty percent of the surface area of the front side of the complementary second pad such that when the two pads are engaged, the touch fasteners and the complementary touch fasteners form a bond of reinforced strength.

According to yet another preferred embodiment of the invention, the vertically spaced strips of touch fasteners and the horizontally spaced strips of complementary touch fasteners include a series of stops for interrupting the separation of the fasteners from each other, including touch fastener material that is sewn to the outer mesh of each pad on one edge only to form a flap that inhibits any attempt to separate the bond formed by the touch fastener material when lifted once contact of the touch fasteners has been made to impede escape of the violent individual once restrained.

According to yet another preferred embodiment of the invention, the touch fasteners and the complementary touch fasteners are perforated to allow the restrained individual to breath through the thickness of the pad underlying the touch fasteners.

According to yet another preferred embodiment of the invention, the first pad and the complementary second pad are constructed of fire-retardant materials.

According to yet another preferred embodiment of the invention, both the first and the complementary second pads of flexible, breathable material are constructed of a plurality of overlaid layers. Each pad includes a layer of dense matting to provide rigidity to the first and the complementary second pads and protection for the attendant against movement of the individual, a layer of soft matting to promote flexibility of the first and the complementary second pads, and an inner layer of mesh to fix the layers and to promote breathability of the first and the complementary second pads.

According to yet another preferred embodiment of the invention, both the first and the complementary second pads include a plurality of pieces of impact-resistant Styrofoam spaced apart from each other along the width and length of each pad within the outer mesh covering of each pad to provide additional kick protection to the attendant while maintaining breathability.

According to yet another preferred embodiment of the invention, the first pad and the complementary second pad are color-coded such that the attendant may easily distinguish between the first pad having touch fasteners and the complementary second pad having complementary touch fasteners.

According to yet another preferred embodiment of the invention, both the first pad and the complementary second pad include a pocket positioned in the outer mesh covering of each pad on the back side thereof for receiving one or more supplemental inserts.

According to yet another preferred embodiment of the invention, the supplemental insert is a bulletproof panel.

BRIEF DESCRIPTION OF THE DRAWINGS

Some of the objects of the invention have been set forth above. Other objects and advantages of the invention will appear as the invention proceeds when taken in conjunction with the following drawings, in which:

FIG. 3 is a top cross-sectional view of the embodiment shown in FIG. 1;

FIG. 4 is a detail view of the hinge represented in the embodiment shown in FIG. 3;

FIG. 6 is a detail view of the stops represented in the embodiment shown in FIG. 5;

DESCRIPTION OF THE PREFERRED EMBODIMENT AND BEST MODE

Figure 1:
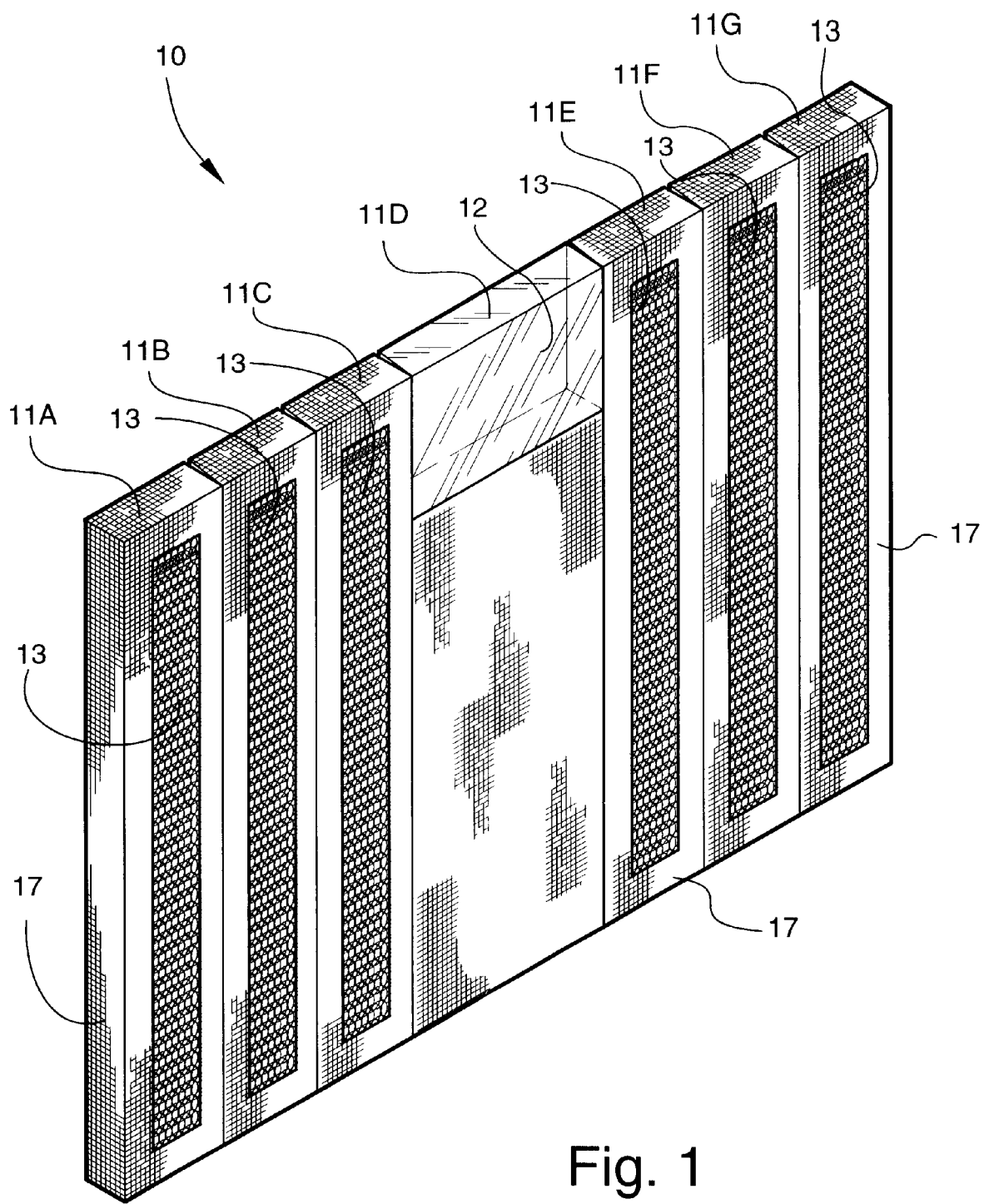
FIG. 1 is a view of the front side of a single pad embodiment of the invention.

Referring now specifically to the drawings, a front view of the physical restraining pad assembly according to the present invention is illustrated in FIG. 1 and shown generally at reference numeral 10. In general, the pad assembly 10 is intended to permit an attendant, or two attendants working together, to restrain a violent individual without injury to the individual or the attendant or attendants. The physical restraining pad assembly 10 is formed from a plurality of joined elongate pads 11A–11G. Each of the pads 11A–G are constructed of flexible, breathable materials, preferably fire-retardant, of a size and shape to collectively cover the body of an individual with arms outstretched. The pad assembly 10 includes a viewing window 12 formed of a clear plastic material of a size and shape to allow the attendant to see through the pad 11D, and observe the individual being restrained. The viewing window may be eliminated and additional padding or protective materials may be substituted when the attendant is otherwise protected, i.e, by a helmet or other protection. Similarly, the viewing window can be customized by size, shape or location to accommodate special needs of the attendants or the client being protected.

As is explained in further detail below, the pads 11A–11G are joined in such a way as to enable the individual being restrained to be wrapped within the pad assembly 10, restrained against a floor or wall with the pad assembly 10 or, with two such pad assemblies 10, to be sandwiched in a retrained position.

As is also shown in FIG. 1, spaced-apart strips of loop touch fasteners 13 are also located on the front side of each of the pads 11A–11C and 11E–11G, i.e, the side facing the individual to be restrained. The strips of touch fasteners 13 preferably include small perforations (not shown) to improve breathability of the pad 11 on the areas where the touch fasteners are placed. The arrangement of the touch fasteners 13 may be any arrangement suitable for the particular use. For example, instead of a long strips of the fasteners 13 as shown in FIG. 1, narrower strips separated by bare areas of padding, or islands of patches may be suitable depending on the type and strength of the touch fasteners and similar considerations.

The pad assembly 10 may also include a panel 15 which may be a kick-resistant or bullet-resistant panel. The panel may be positioned externally on either side of the pad assembly 10, or may be positioned internally, either permanently or removably.

The pad assembly may also be used with a framework mounted on wheels (not shown) by which the pad assembly is moved to and from the point of use. The framework may be, for example, one or more handtrucks. If two or more handtrucks are used, they may be joined by tubing with hinged legs allowing the assembly to stand in a wall or lean-to configuration.

Figure 2:
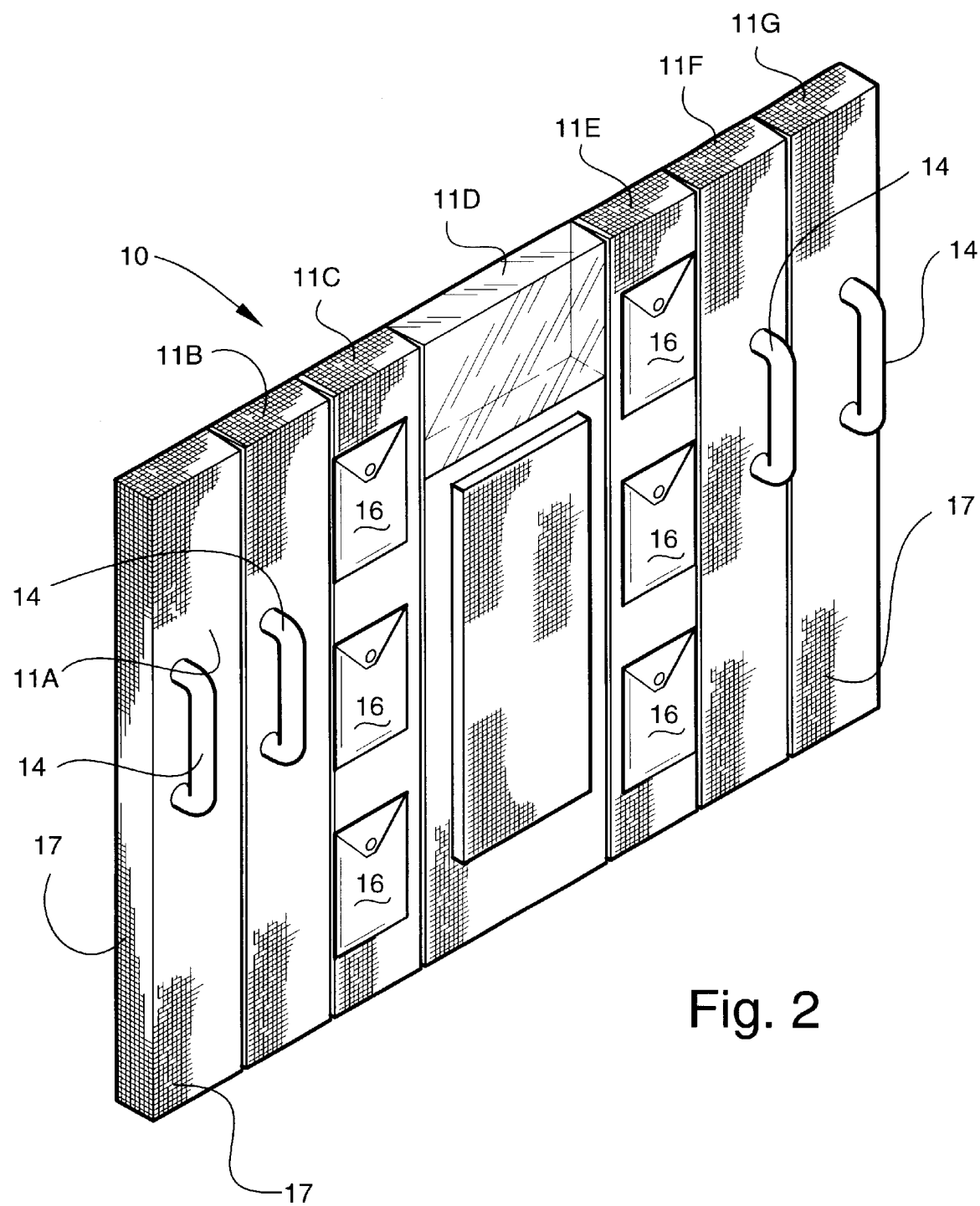
FIG. 2 is a view of the back side of the embodiment shown in FIG. 1.

Referring now to FIG. 2, the rear side of the pad assembly 10 is shown. A pair of spaced handles 14 are positioned to enable an attendant to manoeuver the pad assembly 10 with outstretched arms so in order to infold the individual being restrained. If desired, two or more pairs of handles may be positioned on the rear of the pad assembly 10 in order to accommodate varying arm lengths and heights of different users. The rear of the pad assembly 10 also preferably includes one or more pockets 16 for receiving supplemental inserts, for example, bulletproof inserts, or for holding accessories such as straps.

Each of the pads 11A–11G is formed of a dense, breathable material of compressed polypropylene fibers manufactured generally according to U.S. Pat. Nos. 4,668,562, 4,753,693 and 5,079,074. These patents disclose a dense, resilient, non-woven staple polymer fiber batt formed of either of a plurality of overlaid, relatively thin webs or at least one relatively thick web. The web or webs are comprised at least first and second staple polymer fiber constituents blended to form a homogenous mixture. The first fiber constituent has a relatively low melting temperature and the second fiber constituent has a relatively high melting temperature. The fibers of the first fiber constituent are fused by heat to themselves and to fibers of a second fiber constituent to interconnect the fibers while in a vacuum-compressed state. The heat is sufficient to melt the fibers of the first fiber constituent but not high enough to melt the fibers of the second fiber constituent. Therefore, the fibers of the first fiber constituent retain a plastic memory of the batt in its compressed state to hold the interconnected web layers together at the compressed thickness of the batt, and the fibers of the second fiber constituent retain the plastic memory of the fibers in their non-compressed state to provide substantial resilience.

This padding material may itself be enclosed within a mesh inclosure, for example No. 7 craft mesh. Extreme conditions may necessitate the use of steel mesh, expanded steel or spring steel, for example.

An outer mesh covering 17, for example, Textilene Plus F/R brand mesh material, encloses the entire pad assembly 10.

As is shown in FIGS. 3 and 4, the pads 11A–11G are seamed together with stitches 18 to form hinges which facilitate the ability of the pad assembly 10 to be wrapped around the individual being restrained, and retard the ability of the pad assembly 10 to be bent back on the attendant. A suitable cement may also used to reenforce the seaming.

Figure 5:
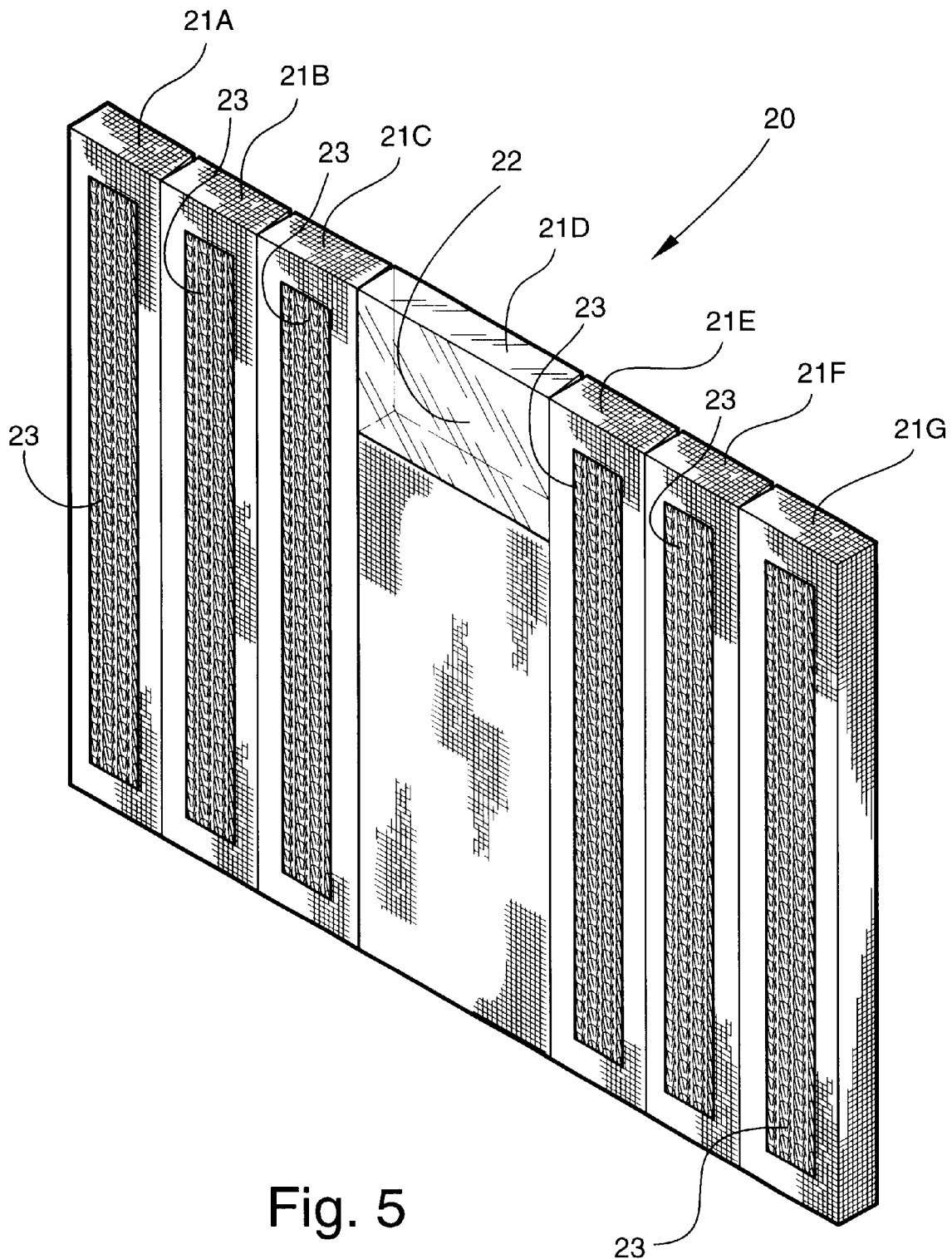
FIG. 5 is a front plan view of the embodiment of the invention which is complementary to the pad shown in FIG. 1.

As is shown in FIG. 5, a pad assembly 20 is formed from a plurality of joined elongate pads 21A–21G. Each of the pads 21A–21G are constructed of flexible, breathable materials, preferably fire-retardant, of a size and shape to collectively cover the body of an individual with arms outstretched. The pad assembly 20 includes a viewing window 22 formed of a clear plastic material of a size and shape to allow the attendant to see through the pad 21D, and observe the individual being restrained. The pads 21A–21G are joined as described above with relation to the pad assembly 10. The pad assembly 20 is intended to be used with pad assembly 10 by two attendants in order to sandwich the individual in a restrained position.

The front side of pads 21A–21G are provided with spaced-apart strips of hook touch fasteners 23 which are positioned to complement and mate with the loop fasteners 13 on the front side of the pad assembly 10. The strips of touch fasteners 23 preferably include small perforations (not shown) to improve breathability of the pad 21 on the areas where the touch fasteners are placed. The arrangement of the touch fasteners 23 may be any arrangement suitable for the particular use. For example, instead of a long strips of the fasteners 23 as shown in FIG. 5, narrower strips separated by bare areas of padding, or islands of patches may be suitable depending on the type and strength of the touch fasteners and similar considerations. Of course, any such arrangement must be compatible for use with the pad assembly 10.

A side elevation of pad assembly 20 is shown in FIG. 6. The rear side of the pad assembly 20 is preferably identical to the rear side of pad assembly 10, is used in the same manner and is therefore not described in further detail. Like elements on the rear side of the pad assembly 20 are shown are shown with the same reference numbers as like elements of the pad assembly 10 in prime notation.

Figure 7:
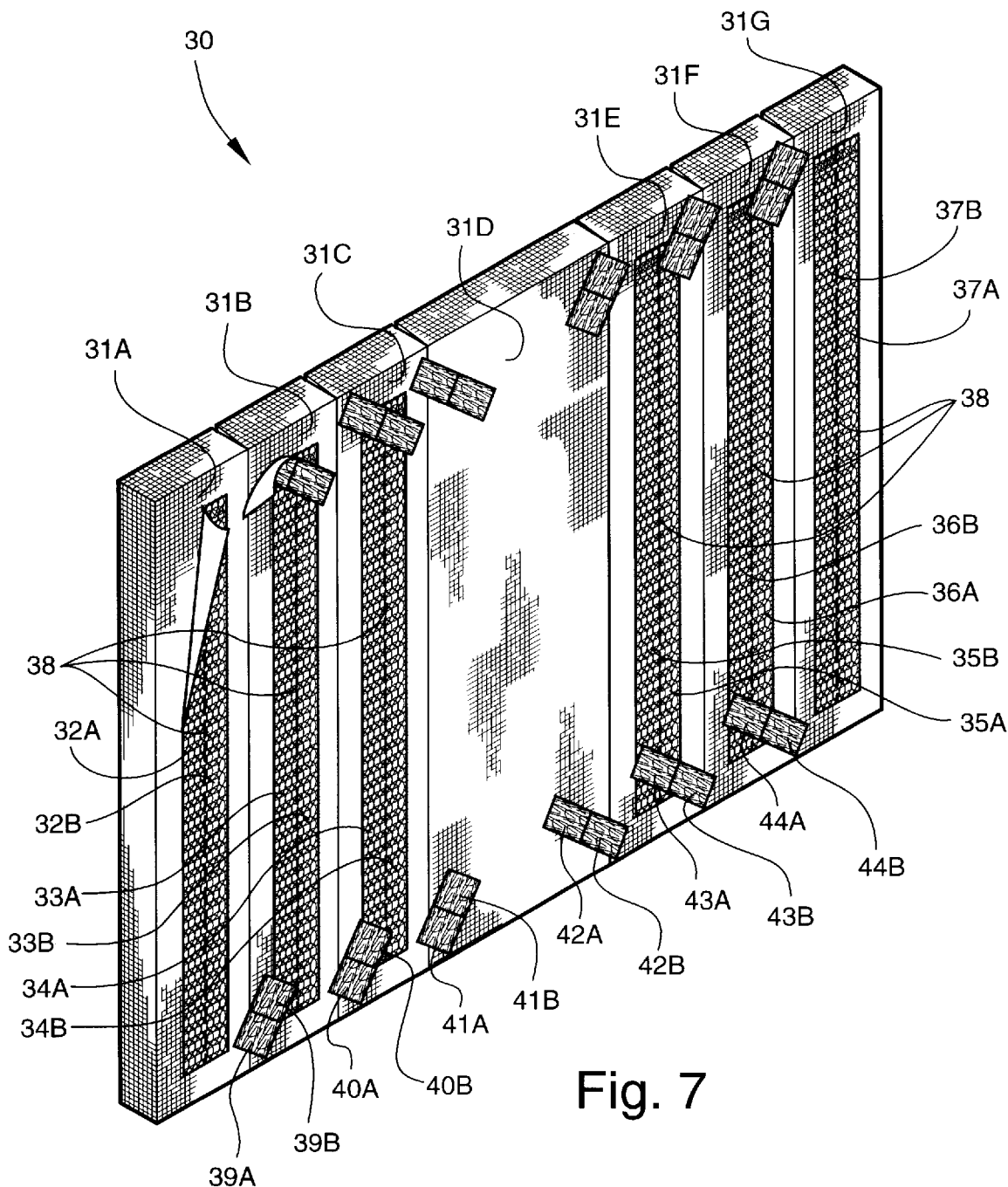
FIG. 7 is an elevation of the front side of an alternate embodiment of one pad assembly.

An alternative embodiment of the pad assembly is illustrated in FIG. 7 and indicated broadly at reference numeral 30. As with the pad assembly 20, the rear side is identical to the rear side of pad assembly 10 and is not described further.

The particular arrangement shown in FIG. 7 is intended for particularly violent and strong individuals and is designed to prevent the individual being restrained from detaching the connected touch fasteners by peeling them away from each other. Specifically, pad assembly 30 includes pads 31A–31G which are joined together as described above with reference to pad assemblies 10 and 20. The front side of the pad assembly includes strips of loop touch fastener material 32–37. The loop touch fastener material 32–37 is divided into two segments 32A,B through 37A,B defined by seams 38. The segments 32A–37A, i.e., the outboard segments, are attached to the surface of the respective pads 31A–31G. The segments 32B–37B, i.e., the inboard segments, are loose and are held to the respective pad 31A–31G by the seams 38.

As is well known, the hook and loop elements of touch fastener material are designed to tightly grip each other and to resist separation in the direction perpendicular to the plane of the base of the material. Separation can normally be achieved by peeling the elements away from each other by application of a shear force with a substantial component parallel or oblique to the plane of the base of the material. To prevent the individual being restrained from accomplishing this peeling action by forcing the attached surfaces of the connected pad assemblies 20 and 30 away from each other, the loose segments 32B–37B will lift off of the face of the pad assembly 30, thus reducing the shearing angle to the point where the force is insufficient to peel the hooks and loops apart. Thus, even if the hooks of the pad assembly 20 separate from the loops on the attached segments 32A–37A, the hooks will not detach from the loose segments 32B–37B.

Additional resistance to peeling separation, particularly in a diagonal direction, can be achieved by providing supplemental loop strips positioned in a diagonal direction. Segments 39A–44A are attached to the surface of the pad assembly 30, while segments 39B–45B are loose and function as described above. An attempt to separate the pad assemblies 20 and 30 by moving one horizontally or vertically relative to the other one would cause the loose segments 39B–45B in the direction opposite the direction of movement to lift away from the surface of the pad assembly 30, thus preventing the shearing action necessary to separate the loops and hooks.

A further illustration of the range of application of the pad assembly according to the invention resides in the use of a single pad assembly of any desired dimension. Hook or other male touch fastener elements are affixed to a rear side of the pad assembly with complementary loops or other female touch fastener elements to a front side of the pad assembly. Restraint of an individual, particularly one of slight build, is accomplished by one attendant who wraps the pad around the subject until the subject is snugly wrapped in the pad with the complementary touch fastener surfaces in contact with each other.

Figure 8:
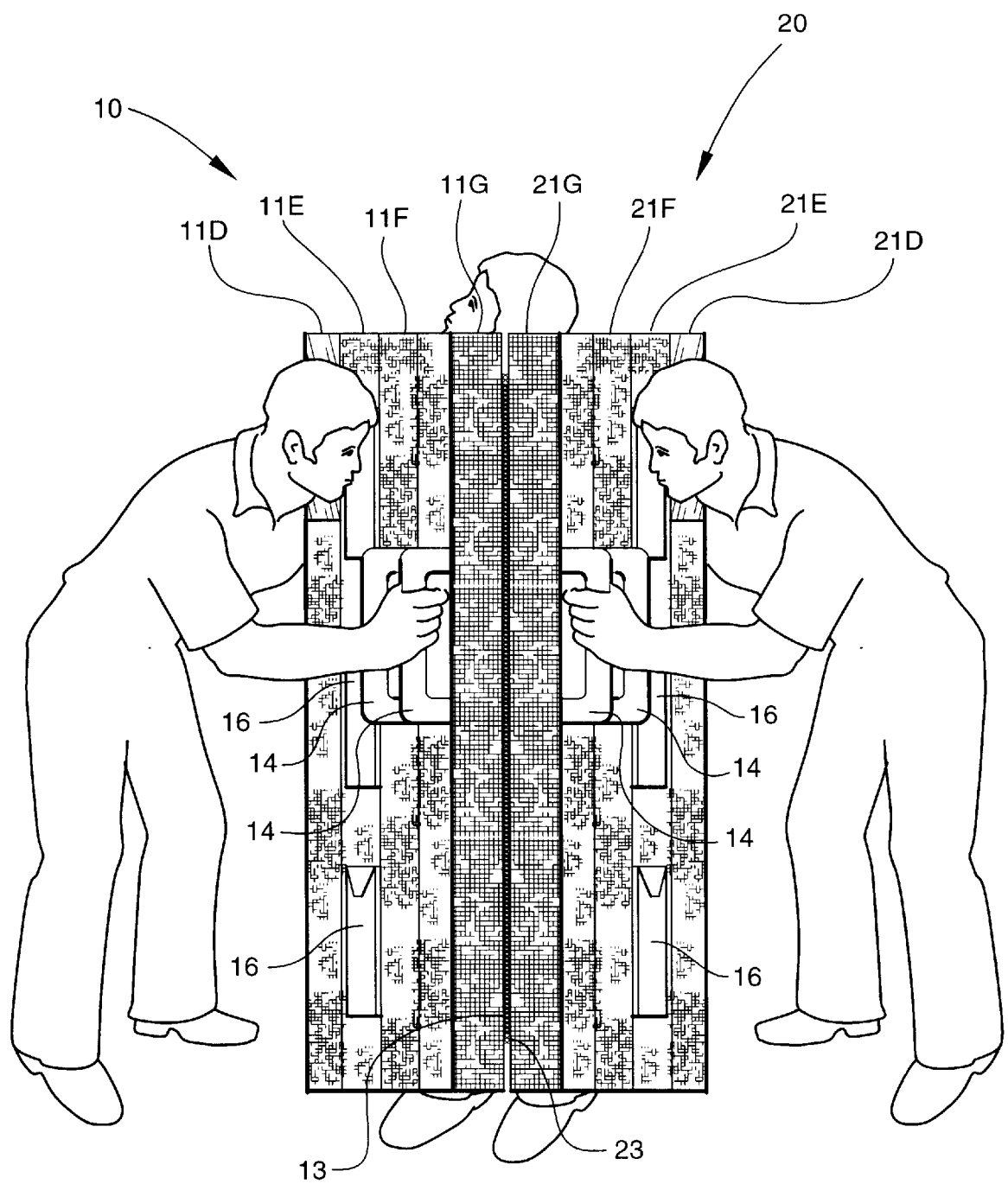
FIG. 8 is a view of an embodiment of the invention showing two of the pads in use.

An illustration of the manner of use of the pad assemblies 10 and 20, or 20 and 30 is shown in FIG. 8.

EXAMPLE

For use in restraining an adult, the pad assemblies 10, 20 or 30 will be approximately 5' in height and 6' in width with a thickness of 2½". Alternately, for use in restraining a child or small adult, the pad assemblies 10, 20 or 30 will be approximately 2' in height and 3' in width with a thickness of 2½'.

A physical restraining pad assembly is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A physical restraining pad assembly for use in restraining a violent individual, comprising:
    (a) a pad constructed of a flexible, breathable material of a size and shape to cover the body of an individual with arms outstretched;
    (b) an outer mesh covering enclosing said pad;
    (c) a plurality of spaced handles positioned on a back side of said pad for use by an attendant; and
    (d) a viewing window of a size and shape to allow the attendant to see through said pad for observing the individual being restrained.

2. The physical restraining pad assembly according to claim 1, wherein the plurality of spaced handles are positioned to accommodate varying arm lengths and heights of different attendants.

3. The physical restraining pad assembly according to claim 1, and including a supplemental head restraining pad positioned adjacent to a top edge of said pad to provide head protection for the individual when restrained.

4. The physical restraining pad assembly according to claim 1, wherein said pad is constructed of fire-retardant materials.

5. The physical restraining pad assembly according to claim 1, wherein the pad of flexible, breathable material is constructed of a plurality of overlaid layers, comprising:
    (a) a layer of dense matting to provide rigidity to said pad and protection for the attendant against movement of the individual;
    (b) a layer of soft matting to promote flexibility of said pad; and
    (c) an inner layer of mesh to fix the layers and to promote breathability of said pad.

6. The physical restraining pad assembly according to claim 1, and including a plurality of pieces of impact-resistance Styrofoam spaced apart from each other along the width and length of the pad within the outer mesh covering of said pad to provide additional kick protection to the attendant while maintaining breathability.

7. The physical restraining pad assembly according to claim 1, and including a pocket positioned within the outer mesh covering of said pad on the back side thereof for receiving one or more supplemental inserts.

8. The physical restraining pad assembly according to claim 7, wherein said supplemental insert comprises a bulletproof panel.

9. A physical restraining pad assembly for use in restraining a violent individual comprising:

(a) a first pad constructed of a flexible, breathable material of a size and shape to cover the body of an individual with arms outstretched, comprising:
  (1) an outer mesh covering enclosing the entire pad;
  (2) touch-fasteners on a front side of said first pad;
  (3) a plurality of spaced handles positioned on a back side of said first pad for use by a first attendant; and
  (4) a viewing window of a size and shape to allow the first attendant to see through said first pad for observing the individual being restrained;
(b) a complementary second pad constructed of a flexible, breathable material of size and shape to cover the body of an individual with arms outstretched for use in conjunction with said first pad in order to confine a violent individual, comprising:
  (1) an outer mesh covering enclosing the entire pad;
  (2) complementary touch fasteners on a front side of said complementary second pad;
  (3) a plurality of handles positioned on a back side of said complementary second pad for use by a second attendant; and
  (4) a viewing window of a size and shape to allow the second attendant to see through said complementary second pad for observing the individual being restrained;
(c) wherein the first attendant manoevers said first pad and the second attendant manoevers said complementary second pad to sandwich a violent individual therebetween such that touch fasteners on the back side of said first pad and the complementary touch fasteners on the back side of said complementary second pad meet to form a bond of sufficient strength to restrain the individual within the remaining space between the two pads where the touch fasteners are not in contact.

10. The physical restraining pad assembly according to claim 9, wherein the plurality of handles are positioned to accommodate varying arm lengths and heights of users.

11. The physical restraining pad assembly according to claim 9, and including a supplemental head restraining pad positioned adjacent to a top edge of each pad to provide head protection for the individual when restrained.

12. The physical restraining pad assembly according to claim 9, wherein the touch fasteners are comprised of spaced-apart strips of touch fasteners located on the front side of said first pad and the complementary touch fasteners are comprised of spaced-apart strips of complementary touch fasteners located on the front side of said complementary second pad, positioned to mate with the spaced-apart strips of touch fasteners when the two pads are pressed together.

13. The physical restraining pad assembly according to claim 9, wherein the touch fasteners are comprised of vertically spaced strips of touch fasteners that occupy at least fifty percent of the surface area of the front side of said first pad and the complementary touch fasteners are comprised of horizontally spaced strips of complementary touch fasteners that occupy at least fifty percent of the surface area of the front side of said complementary second pad such that when the two pads are engaged, the touch fasteners and the complementary touch fasteners will form a bond of reinforced strength.

14. The physical restraining pad assembly according to claim 13, wherein the vertically spaced strips of touch fasteners and the horizontally spaced strips of complementary touch fasteners comprise a series of stops for interrupting the separation of the fasteners from each other, comprising touch fastener material that is sewn to the outer mesh of each pad on one edge only to form a flap that inhibits any attempt to separate the bond formed by the touch fastener material when lifted once contact of the touch fasteners has been made to impede escape of the violent individual once restrained.

15. The physical restraining pad according to claim 9, wherein the touch fasteners and the complementary touch fasteners are perforated to allow the restrained individual to breath through the thickness of the pad underlying the touch fasteners.

16. The physical restraining pad assembly according to claim 9, wherein said first pad and said complementary second pad are constructed of fire-retardant materials.

17. The physical restraining pad assembly according to claim 9, wherein the pad of flexible, breathable material is constructed of a plurality of overlaid layers, each pad comprising:
  (a) a layer of dense matting to provide rigidity to said first and said complementary second pads and protection for the attendant against movement of the individual;
  (b) a layer of soft matting to promote flexibility of said first and said complementary second pads; and
  (c) an inner layer of mesh to fix the layers and to promote breathability of said first and said complementary second pads.

18. The physical restraining pad assembly according to claim 9, and including a plurality of pieces of impact-resistant Styrofoam spaced apart from each other along the width and length of the pad within the outer mesh covering of each pad to provide additional kick protection to the attendant while maintaining breathability.

19. The physical restraining pad assembly according to claim 9, wherein said first pad and said complementary second pad are color-coded such that the attendant may easily distinguish between said first pad having touch fasteners and said complementary second pad having complementary touch fasteners.

20. The physical restraining pad assembly according to claim 9, and including a pocket positioned in the outer mesh covering of each pad on the back side thereof for receiving one or more supplemental inserts.

21. The physical restraining pad assembly according to claim 20, wherein said supplemental insert comprises a bulletproof panel.

* * * * *